United States Patent [19]

Blakely et al.

[11] 4,067,694
[45] Jan. 10, 1978

[54] LOADING AND UNLOADING MECHANISM FOR CONTINUOUSLY ROTATING CONTAINER

[75] Inventors: Robert Bruce Blakely, Rochester; Clyde Leroy Fetterman, Spencerport; Horace Glynn Warren, Hilton, all of N.Y.

[73] Assignee: Eastman Kodak Company, Rochester, N.Y.

[21] Appl. No.: 751,869

[22] Filed: Dec. 17, 1976

[51] Int. Cl.$^2$ .................. G01N 33/16; G01N 1/28; G01N 1/14
[52] U.S. Cl. ........................... 23/253 R; 23/259
[58] Field of Search .............. 23/230 R, 259, 253 R, 23/292; 195/127; 141/130

[56] References Cited

U.S. PATENT DOCUMENTS

| 3,036,893 | 5/1962 | Natelson | 23/230 R |
|---|---|---|---|
| 3,136,609 | 6/1964 | Ciagne | 23/267 |
| 3,193,359 | 7/1965 | Baruch et al. | 23/259 |
| 3,216,804 | 11/1965 | Natelson | 23/253 R |
| 3,219,416 | 11/1965 | Natelson | 23/253 R |
| 3,345,460 | 10/1967 | Betts et al. | 178/7.6 |
| 3,475,130 | 10/1969 | Baruch | 23/253 R |
| 3,489,521 | 1/1970 | Buckle et al. | 23/253 R |
| 3,508,065 | 4/1970 | Holford | 250/219 |
| 3,540,856 | 11/1970 | Rochte et al. | 23/292 |
| 3,545,933 | 12/1970 | Podschady et al. | 23/253 R |
| 3,574,064 | 4/1971 | Binnings et al. | 195/127 |
| 3,575,692 | 4/1971 | Gilford | 23/253 R |
| 3,578,412 | 5/1971 | Martin | 23/259 |
| 3,587,676 | 6/1971 | Ohlin et al. | 23/253 X |
| 3,589,867 | 6/1971 | Heinz et al. | 23/230 R |
| 3,591,249 | 7/1971 | Wildhaber | 250/236 |
| 3,615,236 | 10/1971 | Tamm | 23/253 R |
| 3,616,264 | 10/1971 | Ray et al. | 23/253 R X |
| 3,645,690 | 2/1972 | Rochte et al. | 23/259 X |
| 3,700,911 | 10/1972 | Wildhaber | 250/236 |
| 3,728,227 | 4/1973 | Elson et al. | 195/127 |
| 3,756,920 | 9/1973 | Kelbaugh et al. | 195/127 |
| 3,758,274 | 9/1973 | Ritchie et al. | 23/259 |
| 3,762,879 | 10/1973 | Moran | 23/253 R |
| 3,776,817 | 12/1973 | Van Der Pfordten | 195/103.5 |
| 3,778,129 | 12/1973 | Wildhaber | 250/236 |
| 3,788,816 | 1/1974 | Rohrbaugh et al. | 23/253 R |
| 3,796,544 | 3/1974 | Zavft et al. | 23/259 |
| 3,825,410 | 7/1974 | Bagshawe | 23/230 R |
| 3,832,135 | 8/1974 | Drozdowski et al. | 23/230 R |
| 3,832,140 | 8/1974 | Lorch et al. | 23/259 |
| 3,837,795 | 9/1974 | Becker et al. | 424/3 |

FOREIGN PATENT DOCUMENTS

| 848,287 | 8/1970 | Canada. |
|---|---|---|
| 2,117,341 | 4/1971 | Germany. |

*Primary Examiner*—R.E. Serwin
*Attorney, Agent, or Firm*—Dana M. Schmidt

[57] ABSTRACT

In a continuously rotating container having substrates to be processed, a loading and unloading mechanism is provided which introduces and removes the substrates without interruption of the rotation of the container.

9 Claims, 11 Drawing Figures

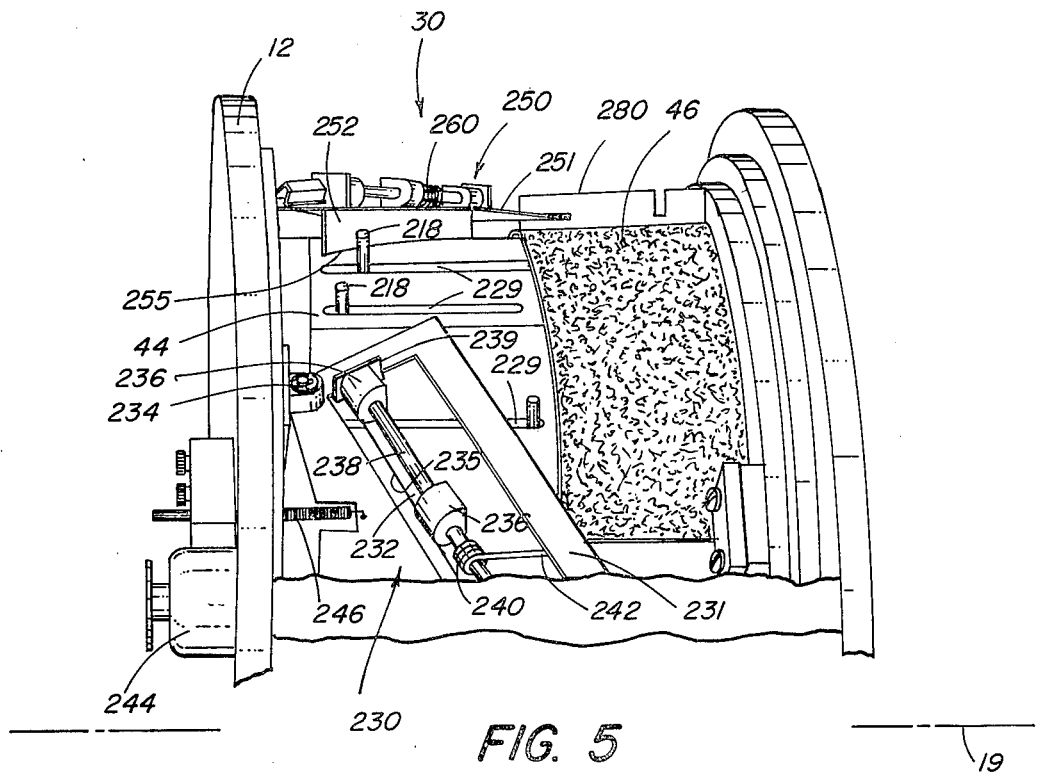
FIG. 5
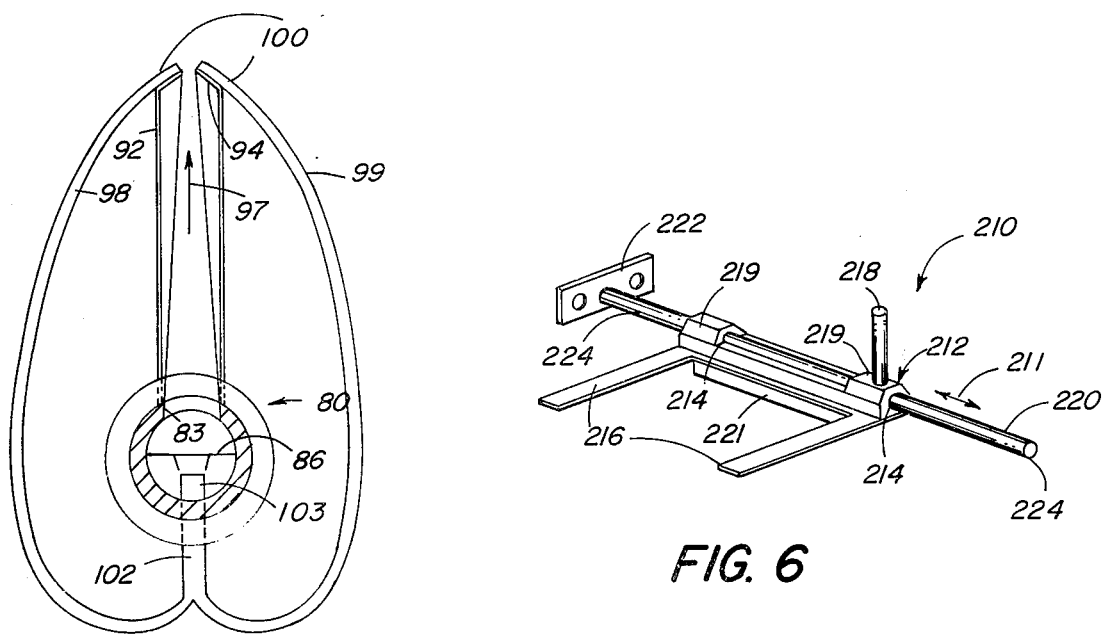
FIG. 2
FIG. 6

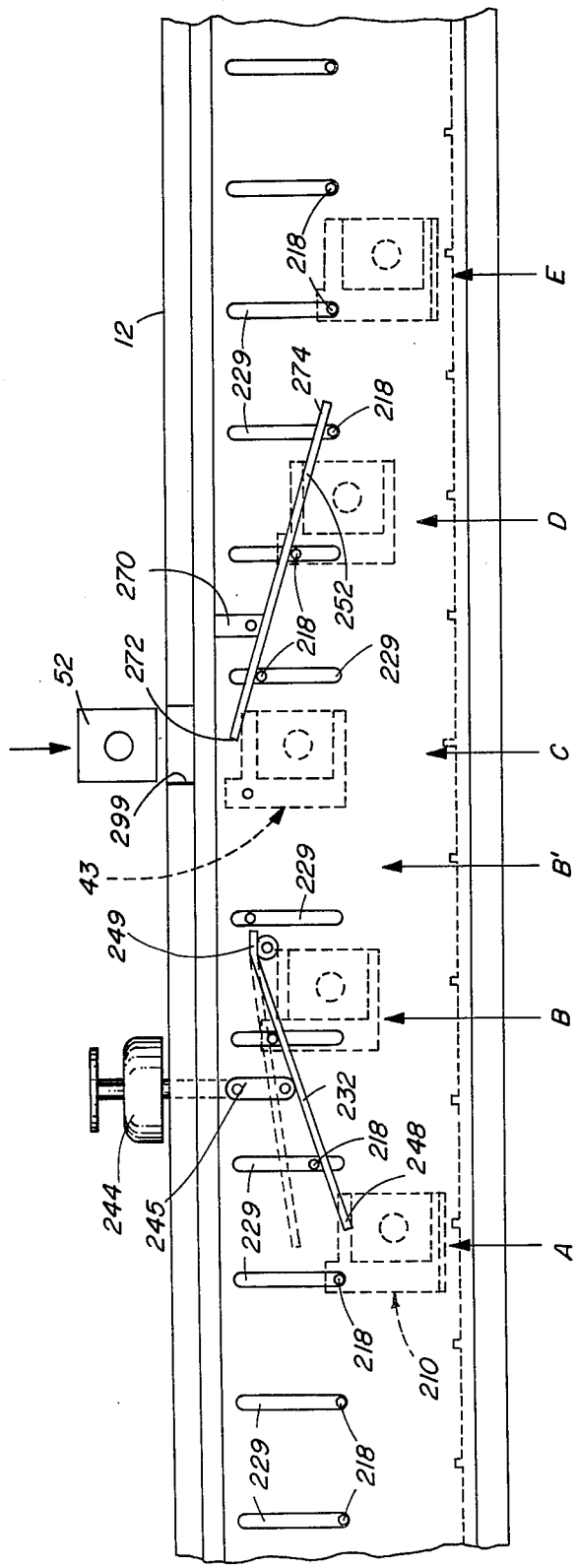

LOADING AND UNLOADING MECHANISM FOR CONTINUOUSLY ROTATING CONTAINER

BACKGROUND OF THE INVENTION

1. Field of the Invention

This invention relates to apparatus for loading and unloading rotating containers such as a radiometric scanner and an incubator incorporating the scanner, useful for detection of the chemical state of a plurality of substrates. In a highly preferred embodiment, while the substrates are held in the container, they are scanned optically to provide a quantitative clinical analysis of blood components.

2. State of the Prior Art

Radiometric scanners cover a wide range of the electromagnetic spectrum. Optical scanners have been used to examine by light the contents of a substrate, such as a printed page. Although such scanners commonly move continuously across the substrate, they are not so limited and include those that obtain a reading without relative motion between the substrate and the sensor.

Some optical scanners have been designed for projecting characters from a single support station or platform, using a light source and a screen, both of which are positioned on the axis of rotation of a lens system which creates sequential light beams, the lens system rotating with respect to the platform. An example is shown in U.S. Pat. No. 3,591,249. Or alternatively the substrate being read can be linearly moved through a plurality of light beams that are discontinuously formed by a lens and mirror system rotating about an axis on which the light source, receptor, and substrate support are positioned, as shown in U.S. Pat. No. 3,345,460. Such devices are not intended fo use, however, in incubators.

Some conventional incubators useful for radiometrically measuring the state of a substrate, usually in liquid form, for clinical analysis generally have a plurality of stations for the substrates, often mounted for rotation about an axis, a temperature control system including a heater, and in some cases a radiometer of some type, such as a reflectometer, designed to selectively scan each of the stations. A relatively simple example of such an incubator is shown in U.S. Pat. No. 3,616,264, whereas devices such as those disclosed in U.S. Pat. No. 3,574,064 illustrate more complex apparatus.

Many clinical analyzers have been provided for liquid substrates, held by cuvettes upon a rotating turntable or conveyer. Although most turntables are intermittently indexed between processing stations, some may be continuously rotated at various speeds. Typical of such devices are those disclosed in U.S. Pat. Nos. 3,193,359; 3,219,416; 3,475,130; 3,489,521; 3,545,933; 3,575,692; 3,578,412; 3,587,676; 3,589,867; 3,615,236; 3,645,690; 3,756,920; 3,758,274; 3,762,879; 3,788,816; 3,796,544; 3,832,135; and 3,832,140. In each of the above, there is no provision for moving the substrate-holding cuvettes in and out of their test location in the turntable while maintaining the turntable's rotation. Generally, loading of the substrate into the cuvettes is achieved by means such as aspirators, used while the turntable is at rest or is at least slowed in its rotation. Such a design causes a delay in processing.

Patents relating only to the general background of scanners or clinical analyzers include U.S. Pat. Nos. 3,508,065; 3,700,911; 3,778,129; 3,776,817; 3,036,893; 3,136,609; 3,216,804; 3,666,076; 3,837,795; 3,825,410; 3,540,856; and 3,728,227, as well as Canadian Pat. No. 848,287 and German OLS No. 2,117,341.

SUMMARY OF THE INVENTION

As an object and advantage of this invention, there is provided an improved apparatus for loading and unloading a rotating container without interrupting the container's rotation.

More specifically, there is provided an improved apparatus including supporting means disposed around a fixed axis for supporting a plurality of substrates; means for sensing the state of the substrates supported by the supporting means; means for continuously rotating at a prescribed speed about the axis the supporting means and the substrates supported thereon; and means for loading and for unloading a substrate into and from engagement with the supporting means. The improvement features the loading and unloading means including a. a stationary loading station;
b. holding means for mating with and holding said substrates, said holding means being disposed for continuous rotation about said axis and for linear movement into and out of positions aligned with said supporting means or with said loading station;
c. and moving means for individually and selectively moving any of said holding means from said supporting means to said loading station and back, said moving means including camming means for moving said any holding means towards said loading station, whereby said any holding means is brought into a mating position with a stationary substrate on said loading station while said any holding member is moving with respect to said loading station, without interrupting the continuous rotation of the apparatus.

By adding a means for controlling the temperature of the substrates, preferably adjacent to each supporting means, the apparatus becomes an incubator providing analysis under controlled temperature conditions.

Other objects and advantages of this invention will become apparent upon reference to the following Description of the Preferred Embodiments, when read in light of the attached drawings.

BRIEF DESCRIPTION OF THE DRAWINGS

FIG. 2 is a sectional view taken generally along line II—II of FIG. 1;

FIG. 5 is a fragmentary, partially-broken-away, perspective view of the loading and unloading mechanism of the invention;

FIG. 6 is an isometric view of a substrate-holding frame;

FIG. 8 is a schematic illustration of the operation of the illustrated embodiment of the invention.

DESCRIPTION OF THE PREFERRED EMBODIMENT

Although the apparatus which is hereinafter described as cooperating with the loading and unloading device of the invention is preferably a radiometric scanner and incubator, it will be realized that the present invention can be utilized to advantage in other analogous or equivalent structures.

A preferred use of the invention is one in which the continuously-rotating container provides a controlled environment for the analysis of generally planar substrates. Those substrates described in Belgian Pat. No. 801,742 granted on Jan. 2, 1974, are particularly suitable, and feature a multi-layered element containing the necessary reagents for reaction with components of blood samples deposited thereon.

Figure 1:
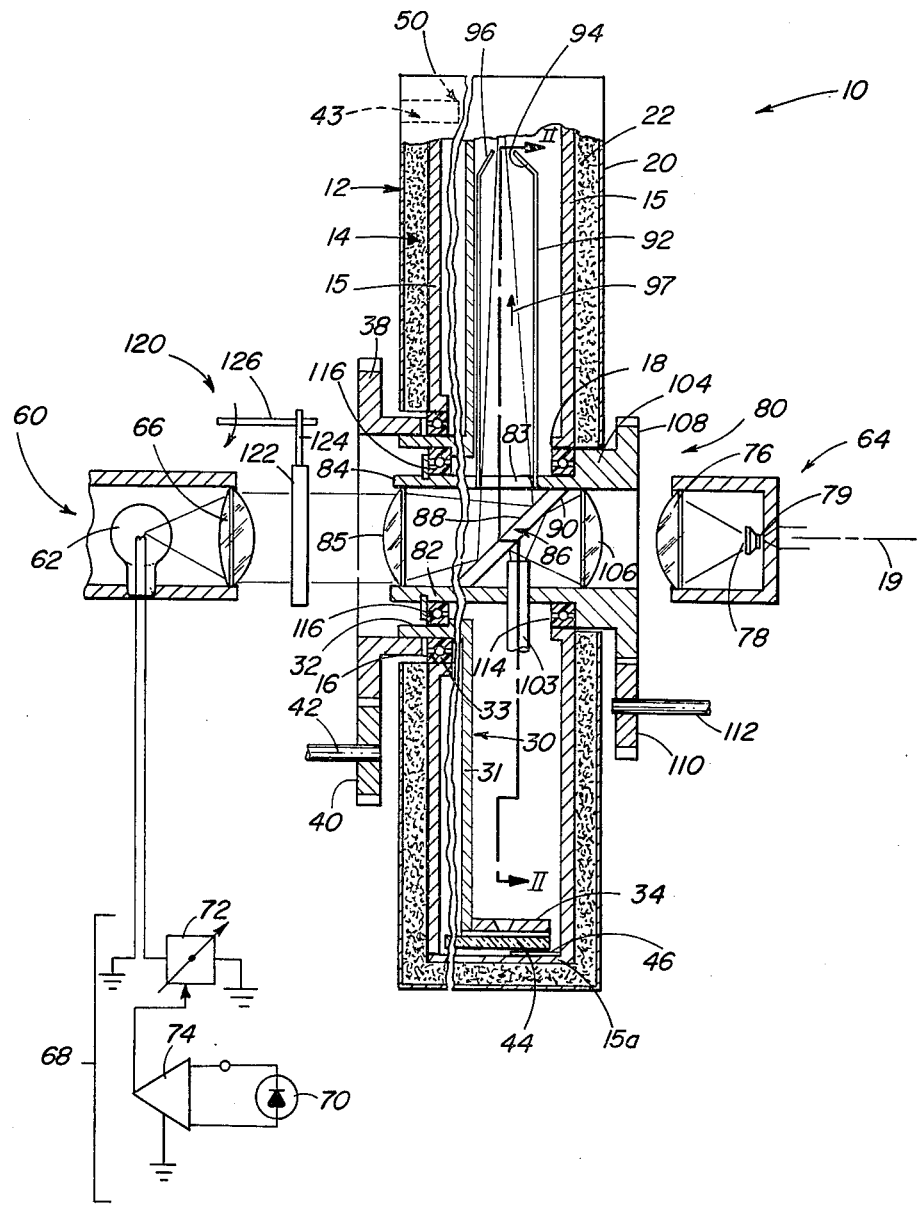
FIG. 1 is a partially schematic, partially fragmented sectional view of one embodiment of apparatus, i.e., a clinical analyzer, in which the present invention is useful.

One such analyzer is illustrated in FIGS. 1 and 2, wherein a continuously rotating container 10, as described and claimed in the commonly owned application of E. Muka, Ser. No. 751,873, filed concurrently herewith, and entitled *Incubator and Radiometric Scanner*, comprises a fixed incubator housing 12, a substrate platform rotor 30, and a radiometer 60, a portion of which is mounted in a rotor 80 separate from rotor 30. It is with this apparatus that means 50 of the invention for loading and unloading substrates 52 onto the platforms are provided, as described in detail hereinafter.

The housing 12 comprises an inner disc 14 having spaced walls 15 and connecting wall 15a, walls 15 being provided each with a circular aperture 16 and 18 concentrically positioned about an axis 19 to accommodate the rotors 30 and 80. An outer wall 20 is provided to form a shield spaced from walls 15, and a layer 22 of insulation can be positioned between the wall 15 and the outer wall 20. Optional conventional heating elements, not shown, can be secured to the inner face of wall 20 to guard against temperature variations that may occur in the environment of use. For this purpose walls 15 and 20 are selected from a material which is a good thermal conductor, such as aluminum.

Mounted for rotation within the housing 12 is rotor 30, comprising a disc portion 31 and a cylindrical bearing sleeve 32 which is either integral with the disc portion, or affixed thereto. Bearings 33 separate the rotor from the housing. Disc portion 31 terminates in a platform ring 34 bearing a plurality of sensing stations or platforms 35, FIG. 3, circumferentially positioned parallel to and substantially equidistant from axis 19 to support the substrates.

To allow access to the substrate by light reflected by the optics as hereinafter described, stations 35 are apertured in a manner sufficient to allow reflected light to be returned to the optics, as hereinafter described.

To rotate each of the stations 35 about axis 19, any suitable means can be provided. As shown in FIG. 1, an annular gear 38 is mounted or otherwise formed on the end of sleeve 32. A mated driving gear 40 mounted on drive shaft 42 engages gear 38 and provides the desired rotation of the stations to move them through a cycle from a stationary loading station 43, FIG. 3.

Figure 3:
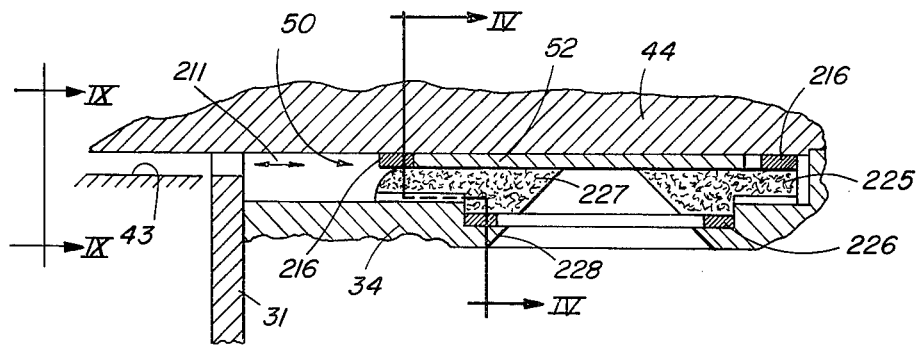
FIG. 3 is an enlarged, fragmentary sectional view of a station of the analyzer shown in FIG. 1, illustrating details of the substrate loading and unloading mechanism.

Spaced away from, but connected to ring 34 is a rotating member 44, preferably in ring form also, FIG. 3. Spaced from member 44 and secured to wall 15a, FIGS. 1 and 5, is a flexible heating pad 46 extending the entire circumference of disc 14, preferably in the form of fixed, high-resistance wires embedded in silicone rubber. To avoid interference with loading means 50, described hereafter, the pad preferably extends only half the axial width of wall 15a.

As noted heretofore, scanning of the substrates is achieved by radiometer 60, which contains an energizing source 62, here an incandescent bulb of suitable radiation, and a sensor 64 for detecting the light reflected from the substrates. The source 62 emits light through a first condenser lens 66, and a servo system 68 monitors the output by conventional circuitry comprising a silicon cell 70 on which a portion of the generated beam of light is deflected by a light pipe, not shown, a suitable, conventional power supply 72, and an amplifier 74. The sensor 64 preferably comprises a cylindrical collection lens 76, filters 78, and conventional, light-detecting silicon cells 79. Both the source and the sensor are preferably located on axis 19, for reasons which will become apparent.

The source 62 and the sensor 64 are illustrated as being fixed with respect to housing 12. However, preferably, some of the optics of the radiometer are mounted on rotor 80 with means providing rotation to the optics both with respect to the fixed housing 12 and with respect to the stations 35. Thus, rotor 80 comprises a cylindrical sleeve 82 having an aperture 83 at about its mid point. One end 84 of the sleeve has within it a second condenser lens 85. Mid-way along sleeve 82 and positioned within it is a reflector 86, shown in FIG. 1 as a planar mirror having two substantially parallel surfaces or sides 88 and 90. Thus sides 88 and 90 become first and second reflectors in the passage of light from source 62 to sensor 64. However, any kind of reflector can be selected, including others such as prisms and fiber-optic bundles comprising light pipes. The active reflector surfaces, namely sides 88 and 90 of mirror 86, are preferably positioned at a 45° angle to axis 19, so as to face towards and away, respectively, from aperture 83. Positioned around aperture 83 is a cylindrical light shield 92, extending radially outwardly from axis 19 to a beveled end 94 which is apertured at its center 96. The effect is to generate a scanning beam from reflector surface 88, shown by arrow 97, that radiates outwardly from axis 19 to the stations 35.

As shown particularly in FIG. 2, also secured to rotor 80 are two light pipes 98 and 99, which have input ends 100 and are optionally joined at 102 to form a common terminus 103. Two such pipes are provided to obtain more optical power. Ends 100 are secured to the exterior of end 94 of the light shield 92, at a position which is at a 45° angle with respect to the incident light reflected perpendicularly to substrates 52, when in position, from mirror surface 88. End 103 directs the collected light, FIG. 1, back to reflector surface 90, which in turn directs the light to a collection lens 106 mounted in end 104 of sleeve 82 opposite to end 84. This lens cooperates with lens 76. An annular gear 108 is secured to or formed as part of sleeve end 104, and driving gear 110 mounted on drive shaft 112 is mated with gear 108, giving rotor 80 and its optical components a drive capability that is independent of the movement of station drive shaft 42. Rotor sleeve 82 rotates with respect to housing 12 by means of bearing 114 positioned between it and housing 12, and with respect to station rotor 30 by means of bearings 116 positioned between it and rotor 30.

To provide multiple read-out capabilities for the radiometer, an optional filter wheel 120 can be provided, comprising a plurality of filters 122, only one of which is shown in FIG. 1, each mounted by an arm 124 on a rotatable drive shaft 126 for movement in and out of the light beam. The filters are selected by appropriate circuitry such that, if fluorescence is to be used, the radiometer becomes a fluorimeter by interposing an appropriate excitation filter, and by the selection of another filter, the radiometer becomes a reflectometer, as is well known.

Lens 76 serves to form the returned, reflected light beam into a cylindrical beam capable of being divided into four parts each for an independent analysis. Thus, the beam can be examined in four sections, each of which is filtered by its own filter 78 having a specified bandpass. Each filtered section of light impinges onto a separate silicon cell 79. Appropriate circuitry can be selected to permit four cells to be switched for separate readings. By switching between these circuits, and therefore between filters, individually selected light frequencies can be considered. Such selectivity is useful not only because certain chemistries being studied in the substrates form indicator dyes that absorb only at certain wavelengths, but also because one of the four filters can be selected to pass only light of a wavelength not absorbed by any indicator dye, thus allowing a control check of the substrate's basic reflectivity.

Typical control circuits for the heating of the incubator include, in addition to heating elements or pads, thermistors positioned adjacent to each heating element to sense temperature changes. Electrical signals therefrom are delivered via amplifiers, such as bridge amplifiers, to conventional temperature control circuits, not shown, operating through transistors to provide current to the heating elements. Preferably, one circuit maintains the temperature of member 44 at about 37° C, while another circuit maintains shield wall 20 at a temperature of about 30° C. Since the circuitry for such temperature controls is conventional, further details are believed to be unnecessary.

It is necessary, of course, that the apparatus determine which sensing station is being scanned. A preferred method incorporates at least one reference mark, not shown, representing a "home" platform, which triggers a response by interrupting a light beam, for example, to a suitable photocell. Such reference techniques are conventional so that further description is unnecessary.

Any type of drive source can be provided for gear 110, including both continuous drives and intermittent drives. The drive mechanism for gear 110, preferably a motor of any suitable type, includes conventional programmable controls such as provide any desired speed or alternate directions of rotation on command with complete search capability, or such drive mechanism can be an incremental motor operating within a fixed predetermined program. A similar drive mechanism, but for continuous rotation only, causes gear 40 to rotate continuously. Full computer control can be used so that the stations of the incubator can be examined in any arbitrary rather than sequential pattern, due to the fact that the drive controls for the two gears 40 and 110 are independent of each other. Thus, where twenty sensing stations numbered 1 through 20 are available, the rates or end-points of the substrate reactions can require that beam 97 be moved, as can be dictated by a computer, to the platforms in this order: 1, 10, 15, 10, 12, 18, 1, 15, 7, 8, 9, 10, 11, 14, 16, 18, etc. In such cases the direction of rotation of the optics may be reversed. Most preferred, however, is an ordered sequence for economy of operation. Circuitry can be provided to discard readings made while both the stations and the beam are rotated, if desired, or such readings can be retained.

Inasmuch as such drive means, their timing diagrams, and the logic circuits providing necessary control are conventional and well-known, further description is unnecessary.

Loading and Unloading Mechanism

In accordance with an important aspect of the invention, to load a substrate 52 into and out of the continuously rotating stations 35, load and unload means 50 comprise, FIGS. 4–8, a retractable frame or substrate-holding means 210, FIG. 6, slidably mounted as shown by arrow 211 on a support rod 220 parallel to the axis 19, moving in and out of the confines of station 35, by the action of camming members 230 and 250. Rod 220 is held in member 44 adjacent each station 35 by a retaining plate 222 at each of the opposed ends 224 of rod 220, FIG. 6. Any kind of substrate holding means 210 can be used, depending upon the size and shape of the substrate being sensed. For rectangular, slide-like substrates 52, means 210 is preferably a frame comprising an elongated body 212 having a bore 214 longitudinally therethrough, to accommodate rod 220, and two spaced-apart fingers or arms 216 extending from one side of the body in a common plane. Fingers 216 are spaced apart a distance sufficient to accommodate a substrate 52, FIG. 3. A camming ear 218 projects generally perpendicularly from body 212 and with respect to the plane of fingers 216. Bore 214 can be a continuous aperture, or a passageway through two shoulders 219, as shown. A substrate pick-up lip 221 preferably depends from body 212 generally perpendicular to fingers 216. The function of frame 210 is to alternately capture or mate with a substrate from a position aligned with a stationary loading station 43, FIG. 3, and to move it to a position aligned with a sensing station 35, as more fully described hereinafter.

Figure 4:
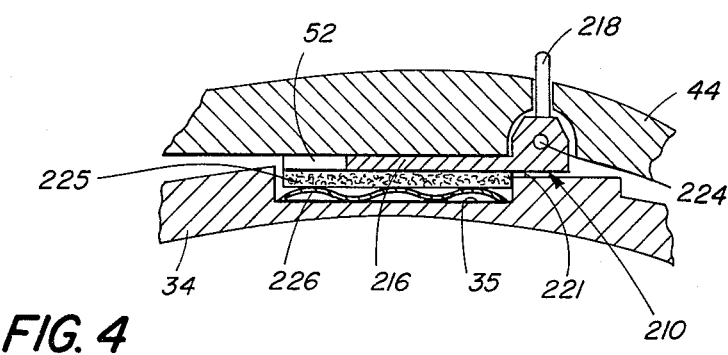
FIG. 4 is a fragmentary sectional view taken generally along the line IV—IV of FIG. 3.

Stations 35 are provided with a pressure pad 225 and a wavy spring ring 226 for holding substrates 52 in proper position against member 44, FIGS. 3 and 4. Both the pads 225 and ring 34 at the stations are given conical apertures 227 and 228, respectively, to allow passage of the incident and reflected light beams.

Figure 7:
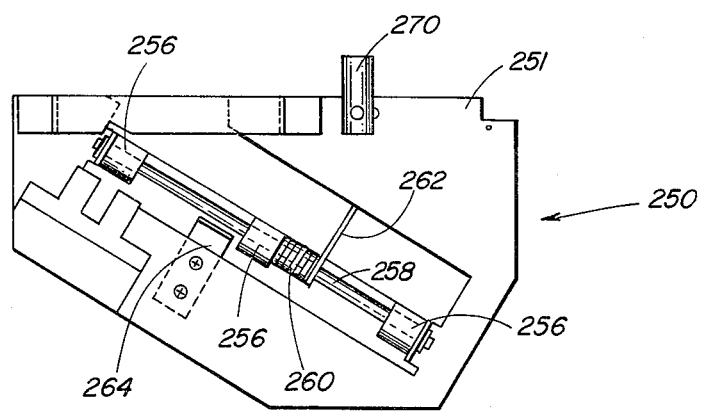
FIG. 7 is a plan view of a camming member shown in FIG. 5.

To move the frame 210 and thus the substrate 52 in and out of the confines of its station 35, member 44 is slotted at 229, FIG. 5, to accommodate the axial movement of ears 218, and movable camming member 230 and fixed camming member 250 are provided, FIGS. 5 and 7, each of which includes cam blades 232 and 252, respectively, which guide ears 218 of frames 210. As shown in FIG. 5, member 230 includes a cam frame 231 pivotally attached to housing 12 by a hinge 234, blade 232 being mounted so as to depend downwardly therefrom towards rotating member 44. Blade 232 has an edge 235, curved to conform to the curvature of member 44. To permit cam blade 232 to pivot out of the way of an ear 218 that might become unable to slide, as when jammed, the blade 232 is pivotally mounted by lugs 236 onto a hinge pin 238 secured to frame 231 at ears 239. A torsion spring 240 wrapped around pin 238 with one free end 242 positioned under frame 231 and the other end (not shown) affixed to the blade, permits the blade to rotate out of the way of a jammed ear, while applying torque that tends to maintain the blade in position against a stop, not shown, where it can engage and cam those ears 218 which are slidable. Alternatively, lugs 236 can be affixed to the pin 238, as can spring 240, and the pin 238 be pivotally mounted in ears 239.

To move cam blade 232 into and out of the generally circular path where ears 218 of frames 210 normally ride, representing the path of substrates held within stations 35, an electrically activated solenoid 244 is provided, FIG. 5. The solenoid acts via a suitable linkage, shown as linkage 245 in FIG. 8, against a return spring 246, secured to housing 12, that holds the cam blade out of such path. Thus, blade 232 is normally skewed with respect to slots 229 so as to be out of the way, as shown in phantom in FIG. 8, of ears 218, but, when pushed by solenoid 244, is moved into the solid-line position in the path of the desired ear 218 to pull it and its frame 210 off the station on which it rides and towards loading station 43. Only that amount of movement sufficient to engage the ear with pick-up end 248 of blade 232 is given to linkage 245 by the solenoid. Trailing end 249 aligns the frame 210 with the loading station 43.

Other electrically actuated devices giving a pulsed linear movement can also be used, in place of the solenoid.

Cam member 250, FIG. 7, is constructed similarly to that of member 230. That is, a cam frame 251 has a hinge pin 258 from which blade 252 movably depends. The blade is affixed to lugs 256 which pivot on pin 258, in a manner similar to cam member 230. Torsion spring 260 wrapped around pin 258 has its free end 262 disposed under frame 251, to normally bias blade 252 against stop 264. As with cam member 230, if a frame 210 is unable to slide back into its station 35, it is necessary that its ear 218 be allowed to continue on a curvilinear path without movement parallel to axis 19. The hinging of blade 252 against spring 260 allows the blade to temporarily rotate out of the way of ear 318.

As shown in FIG. 5, blade 252 also has a curved edge 255, to accommodate the member 44.

Although cam frame 250 can also be hingedly secured to housing 12, it is not necessary. Instead, it is preferably secured by a mounting strap 270, FIGS. 7 and 8, to the housing so that blade 252 is permanently skewed with respect to the normal direction of travel of ears 218. A blade pick-up end 272 is disposed to catch any frame 210 that is at station 43, by ear 218, and carry it all the way back into station 35, where ear 218 clears the trailing end 274 of blade 252. A guide plate 280, FIG. 5, can also be used to support the side of frame 251 opposite to that secured by strap 270.

All of the cam members 230 and 250 and substrate frame 210, as well as the rotor rings 34 and 44, can be manufactured of any suitable material. However, metal is preferred for cam frames 231 and 251, and for the rotor rings.

FIG. 8 further illustrates the sequence of operations identified above. For clarity, the circumference of the incubator has been displayed as though flat, instead of curved as in actual practice. Frames 210, shown in phantom, normally ride within their stations, as shown by position A, where they can be viewed at any time by the scanning beam 97, FIG. 2. In this position, ears 218 are at the innermost end of slots 229. If a certain station, and therefore frame 210, is to be provided with a new substrate 52, cam member 230 and therefore blade 232 is pushed into the path of the desired ear 218 by solenoid 244. The ear and frame are cammed out of the station, as shown at position B, towards loading station 43. A cavity disposed under member 44 immediately before station 43, at position B', FIG. 8, adjacent to the stations 35, allows expended substrates previously incubated and examined to drop out of the frame 210. Any suitable mechanism, not shown, including conventional transport devices, can be used to carry away such expended slides for disposal. In the meantime, a new substrate 52 shown in solid lines has been fed to station 43 through a slot 299 in housing 12, and rests on station 43. Frame 210 catches the substrate between its fingers, position C, and immediately encounters cam blade 252 at its end 272 which forces ear 218 and frame 210, position D, to move back towards its station 35 that has been keeping pace with the frame 210. After ear 218 clears trailing end 274, the frame and therefore the substrate are fully seated within the station between the pressure pad and the heating member, position E.

Unless successive frames 210 are all to be given new substrates, cam blade 232 is pushed into the solid-line position only long enough to pick up the desired frame 210, after which solenoid 244 is released and spring 246, FIG. 5, returns the cam blade 232 to the dotted line position.

The pick-up and trailing ends of the cam blades can be any shape, including curved shape for smoother transition of the movement of ears 218. Portions of the blades between the pick-up and trailing ends can also be non-planar, if desired.

It has been found that the above-described mechanism for loading and unloading substrates will perform satisfactorily even for a rotor operating at speeds up to 12 RPM, handling substrates which are approximately 2 cm square.

Figure 9A:
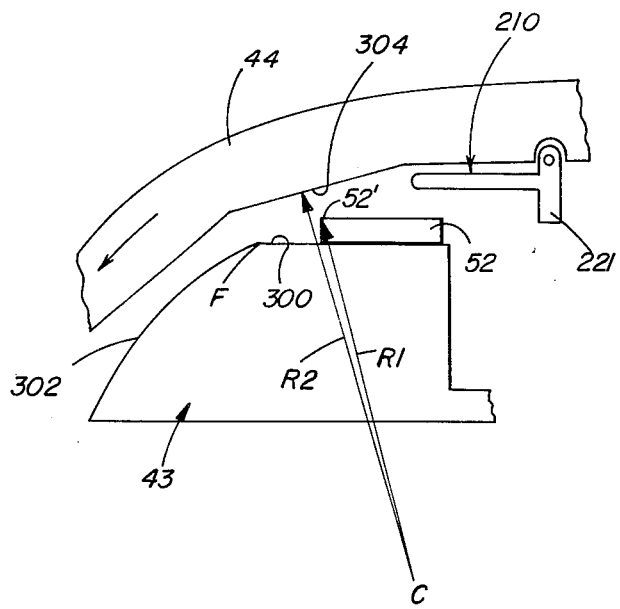
FIGS. 9A through 9C are partially schematic, fragmentary sectional views taken generally along the line IX—IX of FIG. 3.
Figure 9B:
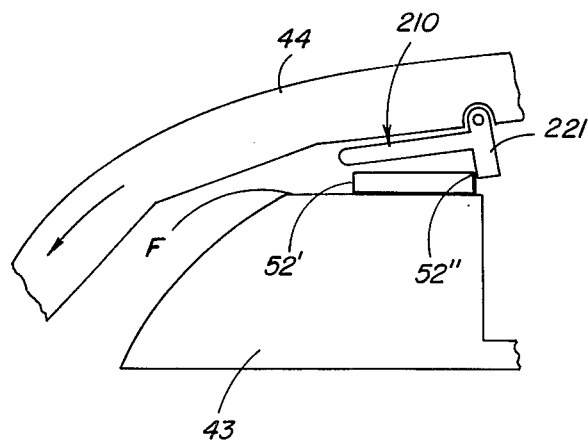
Figure 9C:
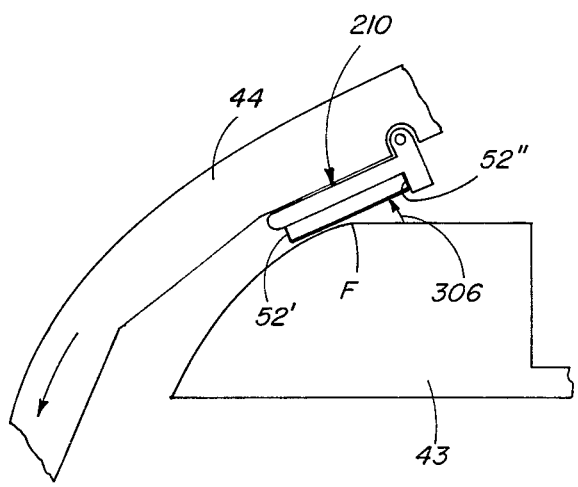

For a preferred, smooth transition of substrate 52 from the fixed station 43, where it is stationary, to the rotating incubator, it is preferable that station 43 be constructed in a manner such as that shown in FIGS. 9A through 9C. That is, station 43 preferably comprises a relatively flat portion 300 terminating in a radius portion 302. The junction between portions 300 and 302 defines a fulcrum "F", the function of which is hereinafter described. The curvature of portion 302 is concentric with the rotating member 44.

The clearance between portion 300 and member 44 is such that, with a substrate 52 stationarily positioned as shown in FIG. 9A, a radius $R_1$ drawn from the center "c" of rotation of member 44 to the leading edge 52' of the substrate 52 is less than a radius $R_2$ drawn to the undersurface of member 44, FIG. 9A. For those constructions, as illustrated, in which said under-surface is a flat face 304, $R_2$ is preferably measured at the face's midpoint. Such a relationship between $R_1$ and $R_2$ insures that a stationary substrate 52 will remain in a nonengaged or cleared position and will not be knocked off by rotating faces 304 before it is properly picked up by the yoke 210 that is sent out from the station 35 that is to receive it.

To raise the substrate from the cleared position shown in FIG. 9A to a position in contact with rotating member 44, a lip 221 extends toward portion 300 a distance sufficient to insure that it will contact the trailing edge 52" of the substrate 52, FIG. 9B, as the desired yoke 210 passes over station 43 to pick up the substrate. At this point, yoke 210 is in the position C shown in FIG. 8. Continued rotation of member 44 causes lip 221 to push substrate 52 over the fulcrum F, and because leading edge 52' of substrate 52 presses against face 304, FIG. 9C, the trailing edge 52" is raised also into contact with face 304, arrow 306. Thus, FIG. 9C, substrate 52 is secured between fingers of yoke 210 in firm contact with rotating member 44, where it is retained as yoke 210 travels back into the incubator through positions D and E, FIG. 8. Radius portion 302 serves to maintain the substrate in registration against member 44 until the substrate moves into engagement with pressure pad 225, FIG. 4.

The invention has been described in detail with particular reference to certain preferred embodiments thereof, but it will be understood that variations and modifications can be effected within the spirit and scope of the invention.

What is claimed is:

1. In apparatus for analysis of a substrate, the apparatus including
   supporting means disposed around a fixed axis for supporting a plurality of substrates;
   means for sensing the state of the substrates supported by said supporting means;
   means for continuously rotating at a prescribed speed about said axis said supporting means and the substrates supported thereon;
   and means for loading and unloading a substrate into and from engagement with said supporting means;
   the improvement wherein said loading and unloading means include,
   a. a stationary loading station;
   b. holding means for mating with and holding said substrates, said holding means being disposed for continuous rotation about said axis and for linear movement into and out of positions aligned with said supporting means or with said loading station;
   c. and moving means for individually and selectively moving any of said holding means from said supporting means to said loading station and back,
   whereby said any holding means is brought into a mating position with a stationary substrate on said loading station while said any holding member is moving with respect to said loading station, without interrupting said continuous rotation.

2. An improved apparatus as defined in claim 1, wherein said holding means include a frame mounted for rotary movement with each of said supporting means.

3. An improved apparatus as defined in claim 2, wherein said frame includes fingers spaced apart a distance sufficient to accommodate a substrate therebetween, and further including a rod adjacent said supporting means and extending generally parallel to said axis, said frame being mounted for reciprocal movement on said rod.

4. An improved apparatus as defined in claim 1, and further including camming means for moving said any holding means towards said loading station, said moving means including means for moving said camming means towards and away from any one of said holding means which is aligned with said supporting means.

5. An improved apparatus as defined in claim 1, and further including temperature control means located adjacent to said supporting means for maintaining a desired temperature.

6. An improved apparatus as defined in claim 1, and further including means for raising a substrate on said loading station from a position in which it is clear of said rotated supporting means, to a position in which it is engaged by said supporting means.

7. An improved apparatus as defined in claim 6, wherein said loading station includes a relatively flat portion at which said substrate is in a nonengaged position, and wherein said raising means includes a curved, radius portion of said station joining said flat portion at an edge defining a fulcrum over which the substrate rides as it is mated with said holding means.

8. In apparatus for analysis of a substrate, the apparatus including
   supporting means disposed around a fixed axis for supporting a plurality of substrates;
   means for sensing the state of the substrates supported by said supporting means;
   means for continuously rotating at a prescribed speed about said axis said supporting means and the substrates supported thereon;
   and means for loading and unloading a substrate into and from engagement with said supporting means;
   the improvement wherein said loading and unloading means include,
   a. a stationary loading station spaced away from said supporting means along a line parallel to said axis;
   b. a plurality of frames mounted for rotary movement with each of said supporting means, each of said frames having fingers spaced apart a distance sufficient to accommodate a substrate therebetween;
   c. a plurality of rods adjacent said supporting means, each extending generally parallel to said axis, said frames being slidable on said rods between positions aligned with said supporting means or said loading station;
   d. and camming means for individually and selectively moving any of said frames towards and away from said loading station,
   whereby substrates are loaded from said loading station to said supporting means without interrupting said continuous rotation.

9. An improved apparatus as defined in claim 8, and further including means for moving a portion of said camming means towards and away from said holding means when they are aligned with said supporting means.

* * * * *